(12) United States Patent
Baer (10) Patent No.: US 10,228,384 B2
(45) Date of Patent: Mar. 12, 2019

(54) METHOD OF ROTATING A SAMPLE CONTAINER CARRIER, LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Jonathan Baer, Stuttgart (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 58 days.

(21) Appl. No.: 15/278,252

(22) Filed: Sep. 28, 2016

(65) Prior Publication Data

US 2017/0108522 A1   Apr. 20, 2017

(30) Foreign Application Priority Data

Oct. 14, 2015   (EP) .................................... 15189847

(51) Int. Cl.
| | |
|---|---|
| *G01N 35/04* | (2006.01) |
| *B65G 47/244* | (2006.01) |
| *G01N 35/00* | (2006.01) |
| *B65G 54/02* | (2006.01) |

(52) U.S. Cl.
CPC ........... *G01N 35/04* (2013.01); *B65G 47/244* (2013.01); *B65G 47/2445* (2013.01); *B65G 54/02* (2013.01); *B65G 54/025* (2013.01); *G01N 35/00722* (2013.01); *G01N 35/00732* (2013.01); *G01N 2035/00752* (2013.01); *G01N 2035/0475* (2013.01); *G01N 2035/0477* (2013.01); *G01N 2035/0482* (2013.01); *G01N 2035/0489* (2013.01)

(58) Field of Classification Search
CPC ....... B65G 47/244; G01N 2035/00752; G01N 2035/0475; G01N 2035/0482; G01N 35/00722; G01N 35/00732; G01N 35/04
See application file for complete search history.

(56) References Cited

U.S. PATENT DOCUMENTS

| | | | |
|---|---|---|---|
| 3,273,727 | A | 9/1966 | Rogers et al. |
| 3,653,485 | A | 4/1972 | Donlon |
| 3,901,656 | A | 8/1975 | Durkos et al. |
| 4,150,666 | A | 4/1979 | Brush |
| 4,395,164 | A | 7/1983 | Beltrop et al. |
| 4,544,068 | A | 10/1985 | Cohen |
| 4,771,237 | A | 9/1988 | Daley |
| 5,120,506 | A | 6/1992 | Saito et al. |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Samuel P Siefke
(74) *Attorney, Agent, or Firm* — Roche Diagnostics Operations, Inc.

(57) ABSTRACT

A method of rotating a sample container carrier on a transport plane of a laboratory sample distribution system is presented. The sample container carrier is rotated by using a movement relative to a number of rotator elements. A laboratory sample distribution system being able to perform such a method and a laboratory automation system comprising such a laboratory sample distribution system are also presented.

10 Claims, 3 Drawing Sheets

(56) References Cited

U.S. PATENT DOCUMENTS

| | | | |
|---|---|---|---|
| 5,295,570 A | 3/1994 | Grecksch et al. |
| 5,309,049 A | 5/1994 | Kawada et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,810,706 B2 | 11/2017 | Riether et al. |
| 2002/0009391 A1 | 1/2002 | Marquiss et al. |
| 2003/0089581 A1* | 5/2003 | Thompson ............. B65G 23/18 198/619 |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0037709 A1 | 2/2006 | Itoh |
| 2006/0047303 A1 | 3/2006 | Ortiz et al. |
| 2006/0219524 A1 | 10/2006 | Kelly |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234065 A1 | 8/2014 | Heise et al. |
| 2014/0234949 A1 | 8/2014 | Wasson et al. |
| 2014/0234978 A1 | 8/2014 | Heise et al. |
| 2015/0014125 A1 | 1/2015 | Hecht |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276781 A1 | 10/2015 | Riether et al. |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |

(56) References Cited

U.S. PATENT DOCUMENTS

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A2 | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A2 | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A2 | 2/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/0087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/152089 A1 | 10/2013 |
| WO | 2013/169778 A1 | 11/2013 |
| WO | 2013/177163 A1 | 11/2013 |
| WO | 2014/059134 A1 | 4/2014 |
| WO | 2014/071214 A1 | 5/2014 |

* cited by examiner

Fig. 4

000
METHOD OF ROTATING A SAMPLE CONTAINER CARRIER, LABORATORY SAMPLE DISTRIBUTION SYSTEM AND LABORATORY AUTOMATION SYSTEM

CROSS-REFERENCE TO RELATED APPLICATIONS

This application claims priority to EP 15189847.5, filed Oct. 14, 2015, which is hereby incorporated by reference.

BACKGROUND

The present disclosure generally relates to a method of rotating a sample container carrier of a laboratory sample distribution system, to a laboratory sample distribution system and to a laboratory automation system comprising a laboratory sample distribution system.

Known laboratory sample distribution systems are typically used in laboratory automation systems in order to transport samples contained in sample containers between different laboratory stations.

A typical laboratory sample distribution system provides for a high throughput and for reliable operation. In order to identify sample containers that are transported by a laboratory sample distribution system, these sample containers are typically marked with barcodes. Such barcodes can be read using barcode reading devices.

While identification of sample containers using barcodes is, in principle, a reliable and simple method for identification, it has been recognized that a specific problem arises in laboratory sample distribution systems when barcodes do not extend over a whole horizontal circumference of a sample container, because a barcode reading device has typically only the ability to detect less than 180° of a sample container. Thus, there arises a need for ensuring that barcodes can be read reliably in a laboratory sample distribution system.

Therefore, there is a need for a method to simplify readout of barcodes independently of its circumferential coverage.

SUMMARY

According to the present disclosure, a method of rotating a sample container carrier of a laboratory sample distribution system is presented. The laboratory sample distribution system can comprise a number of sample container carriers. The sample container carriers can be adapted to carry one or more sample containers. The sample containers can comprise samples. The laboratory sample distribution system can also comprise a transport plane. The transport plane can be adapted to support the sample container carriers. The laboratory sample distribution system can also comprise a driver. The driver can be adapted to move the sample container carriers on top of the transport plane. The laboratory sample distribution system can also comprise a control device. The control device can be configured to control the driver such that the sample container carriers move over the transport plane along predetermined transport paths. The method can comprise the steps: a) moving the sample container carrier and/or a rotator element comprising a linear surface relative to each other on the transport plane such that the sample container carrier abuts the linear surface and b) moving the sample container carrier and/or the rotator element relative to each other on the transport plane such that the linear surface exerts a rotating force on the sample container carrier.

Accordingly, it is a feature of the embodiments of the present disclosure to provide for a method to simplify readout of barcodes independently of its circumferential coverage. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method of rotating a sample container carrier of a laboratory sample distribution system is presented.

The laboratory sample distribution system can comprise a number of sample container carriers. The sample container carriers can be adapted to carry one or more sample containers. The sample containers can comprise laboratory samples.

The laboratory sample distribution system can further comprise a transport plane. The transport plane can be adapted to support the sample container carriers.

The laboratory sample distribution system can further comprise a driver. The driver can be adapted to move the sample container carriers in two dimensions on top of the transport plane.

The laboratory sample distribution system can further comprise a control device. The control device can be configured to control the driver such that the sample container carriers move over the transport plane along predetermined transport paths. The control device can be adapted to activate the driver such that the sample container carriers move simultaneously and independently from one another along pre-calculated routes.

The method can comprise the following steps a) moving the sample container carrier to be rotated and/or a (first) rotator element comprising a (first) linear and/or planar surface relative to each other on the transport plane, e.g. along linear paths, such that (until) the sample container carrier abuts (is in contact with) the linear and/or planar surface, and b) linearly and/or translatory, moving the sample container carrier and/or the (first) rotator element relative to each other on the transport plane, such that the (first) linear surface exerts a rotating force on the sample container carrier.

A sample container carrier can e.g. be rotated until a sample container carried by the sample container carrier is oriented such that a barcode placed on the sample container can be read by a barcode reading device.

For performing the method, only the sample container carrier itself and a rotator element may be needed.

According to an embodiment, the sample container carrier can have a circular horizontal cross-section, especially in a plane substantially parallel to the transport plane. This can allow for easy and smooth rotation of the sample container carrier.

According to an embodiment, in step b, the rotator element can move on the transport plane while the sample container carrier can be held in a constant position on the transport plane. In other words, the sample container carrier may not move translatory while being rotated.

According to an embodiment, in step a, a further (second) rotator element comprising a further (second) linear surface ican be moved on the transport plane such that (until) the sample container carrier abuts (is in contact with) the further (second) linear surface. In step b, the further (second) rotator element can be moved relative to the sample container carrier such that the further (second) linear surface can exert a further (second) rotating force on the sample container carrier, the further (second) rotating force amplifying the (first) rotating force.

Using the further (second) rotator element, the sample container carrier can be rotated by not only one, but two rotator elements. This can provide for a smoother operation and for clamping or fixation of the sample container carrier between the two rotator elements. A drifting of the sample container carrier can thus be prevented.

According to an embodiment, the further rotator element can be moved and held substantially parallel to the rotator element. This can lead to a defined exertion of the (first) rotating force and the further (second) rotating force.

According to an embodiment, the further (second) rotator element can be moved such that the further (second) rotating force can have the same magnitude as the (first) rotating force. This can, for example, be achieved by moving the two rotator elements with the same speed.

According to an embodiment, in step b, the sample container carrier can move on the transport plane relative to the rotator element while the rotator element can be held in a constant position on or besides (adjacent to) the transport plane. In this embodiment, the rotator element can be held fixed and does not have to comprise a means for moving it on the transport plane.

It can be noted that it can also be possible to move both the sample container carrier and the rotator element simultaneously in order to exert the rotating force.

According to an embodiment, each linear surface can define a plane which can be substantially perpendicular to the transport plane. This can provide for a good mechanical contact between the linear surface and the sample container carrier.

Alternatively, the linear or planar surface of the rotator element may define a plane or may be a plane, or area, substantially parallel to or lying in the transport plane. The linear or planar surface of the rotator element may be part of the transport plane. The linear or planar surface of the rotator element being part of the transport plane may have a coefficient of friction differing from a coefficient of friction of the remaining transport plane. By moving the sample container carrier partially over the linear or planar surface of the rotator element, the rotating force can be exerted due to the different coefficients of friction.

According to some embodiments, each linear surface can be a knurled, toothed or rubber-coated surface. According to further embodiments, the sample container carrier can have a knurled, toothed or rubber-coated outer surface abutting or being intended to be in contact with the linear surface. By such measures, friction between the linear surface and the sample container carrier can be significantly increased, which can ease operation when rotating the sample container carrier.

According to an embodiment, the sample container carrier can be rotated in step b in a field of view of a barcode reading device until a barcode located on the sample container or on the sample container carriercan be facing towards the barcode reading device. Thus, the barcode can be read easily and reliably by the barcode reading device.

A laboratory sample distribution system is presented. The laboratory sample distribution system can comprise a number of sample container carriers. The sample container carriers can be adapted to carry one or more sample containers. The sample containers can comprise laboratory samples to be analyzed by laboratory stations.

The laboratory sample distribution system can further comprise a transport plane. The transport plane can be adapted to support the sample container carriers.

The laboratory sample distribution system can further comprise a driver. The driver can be adapted to move the sample container carriers on top of the transport plane.

The laboratory sample distribution system can further comprise a control device (e.g. microprocessor and corresponding software and hardware). The control device can be configured to control the driver such that the sample container carriers can move over the transport plane along predetermined transport paths. The control device can also be configured to activate the driver such that the sample container carriers can move simultaneously and independently from one another along pre-calculated routes.

The laboratory sample distribution system can further comprise at least one rotator element comprising a linear or planar surface. Furthermore, the control device can be configured to perform a method according to the present disclosure.

By the laboratory sample distribution system, a sample container, or a sample container carrier, can be rotated, e.g. such that a barcode or another identification element located on the sample container, or the sample container carrier, can be easily read, for example, by a barcode reading device.

According to an embodiment, each sample container carrier and/or each rotator element can comprise a number (e.g. 1 to 10) of magnetically active devices, e.g. incorporated as permanent magnets. The rotator element may comprise two magnetically active devices. In such an embodiment, the driver may be embodied as electro-magnetic actuators such that a magnetic drive force can be applied to the sample container carriers and/or to the rotator elements.

According to an alternative embodiment, the driver may be embodied as a number of wheels driven by electric motors comprised by each sample container carrier and/or each rotator element and controllable by the control device. This can allow for self-propelled sample container carriers and/or rotator elements which can omit the need for electro-magnetic actuators or other external parts for the driver.

According to an embodiment, the laboratory sample distribution system can comprise a barcode reading device having a field of view. The control device can be configured to perform the disclosed method such that the sample container carrier can be rotated in the field of view. Thus, the sample container carrier can be moved into the field of view of the barcode reading device without taking care of its orientation. Once it is in the field of view, the disclosed method can be performed in order to rotate the sample container carrier such that a barcode can be read by the barcode reading device. As there is no further need for transportation until the barcode will be read, an inadvertent rotation of the sample container carrier that could decrease visibility of the barcode may not take place.

The sample containers can typically be designed as tubes made of glass or transparent plastic and can typically have an opening at an upper end. The sample containers can be used to contain, store and transport samples such as blood samples or chemical samples.

The transport plane can also be denoted as transport surface. The transport plane can support the sample container carriers, what can also be denoted as carrying the sample container carriers.

The electro-magnetic actuators can typically be built as electromagnets, having a solenoid surrounding a ferromagnetic core. These electro-magnetic actuators may be energized in order to provide for a magnetic field that can be used to move or drive the sample container carriers and the rotator element(s). For that purpose, the at least one magnetically active device in each sample container carrier and/or rotator element may be a permanent magnet. Alternatively or additionally, an electromagnet can be used.

The control device can typically be a microprocessor, a microcontroller, a field programmable gate array, a standard computer, or a similar device. In a typical embodiment, the control device can comprise a processor and storage. Program code can be stored in the storage in order to control the behavior of the processor when the program code is executed by the processor.

The sample container carriers can typically be adapted to move in two dimensions on the transport plane. For that purpose, the electro-magnetic actuators may be arranged in two dimensions below the transport plane. The electro-magnetic actuators may be arranged in a grid, or matrix, having rows and columns along which the electro-magnetic actuators can be arranged.

A laboratory automation system is also presented. The laboratory automation system can comprise a number of laboratory stations such as, for example, pre-analytical, analytical and/or post-analytical stations. It can further comprise a laboratory sample distribution system adapted to distribute sample container carriers between the laboratory stations.

The laboratory stations may be arranged adjacent to the laboratory sample distribution system.

Pre-analytical stations may be adapted to perform any kind of pre-processing of samples, sample containers and/or sample container carriers.

Analytical stations may be adapted to use a sample or part of the sample and a reagent to generate a measured signal, the measured signal indicating if and in which concentration, if any, an analyte is existing.

Post-analytical stations may be adapted to perform any kind of post-processing of the samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

Figure 1:
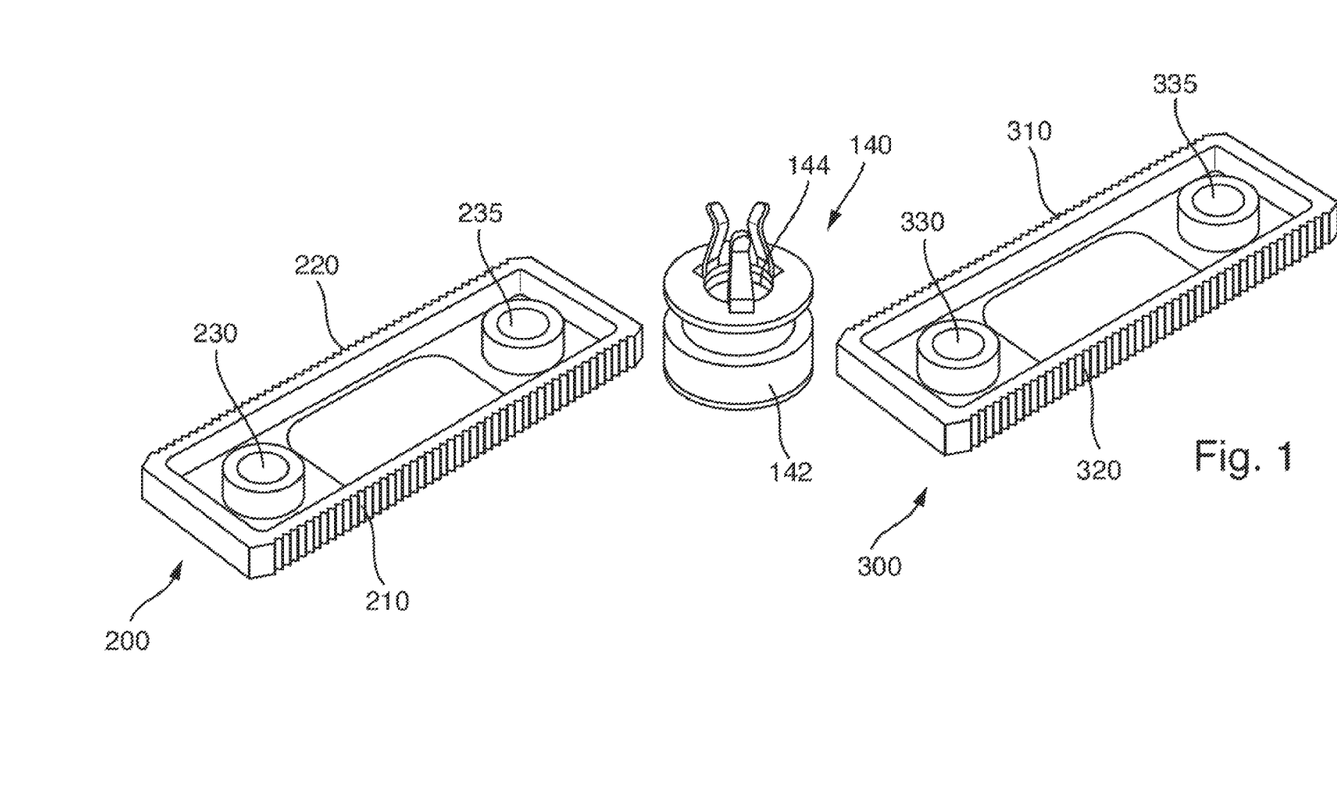
FIG. 1 illustrates an arrangement of a sample container carrier together with two rotator elements according to an embodiment of the present disclosure.

Referring initially to FIG. 1, FIG. 1 shows an arrangement of a sample container carrier 140, a first rotator element 200 and a second rotator element 300. The sample container carrier 140 can have a circular horizontal cross-section. It can comprise an outer surface 142 having the shape of a cylinder. It can further comprise a sample container receiver 144 adapted to receive and support a sample container for transport on a transport plane.

The first rotator element 200 can comprise a first linear surface 210 and a second linear surface 220. Both linear surfaces 210, 220 can be oriented along a substantially straight line. Furthermore, the linear surfaces 210, 220 can be toothed. The first rotator element 200 can further comprise a first magnetically active device 230 and a second magnetically active device 235. The magnetically active devices 230, 235 can be embodied as permanent magnets. The first and second rotator element 200 and 300 can be identically embodied, i.e. the second rotator element 300 accordingly can comprise a first linear surface 310 and a second linear surface 320. Both linear surfaces 310, 320 can be oriented along a substantially straight line. Furthermore, the linear surfaces 310, 320 can be toothed. The second rotator element 300 can further comprise a first magnetically active device 330 and a second magnetically active device 335. The magnetically active devices 330, 335 can be embodied as permanent magnets.

Figure 2:
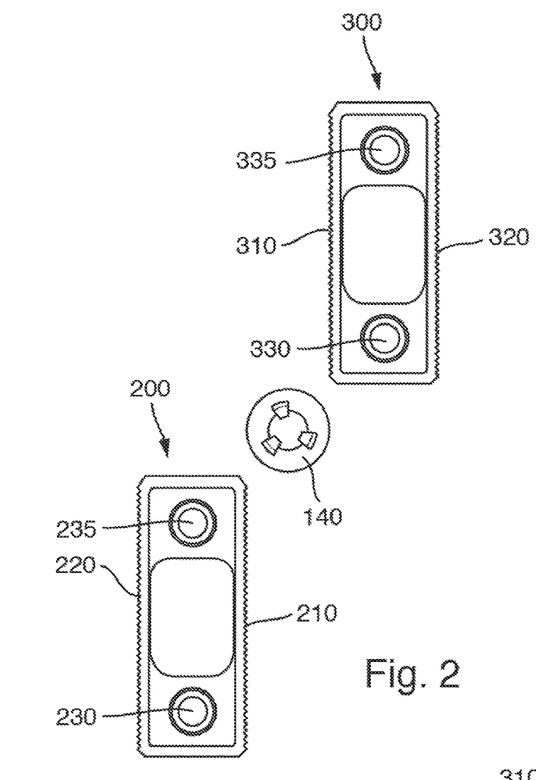
FIG. 2 illustrates the arrangement of FIG. 1 in a top view according to an embodiment of the present disclosure.

FIG. 2 shows the arrangement of FIG. 1 in a top view.

Figure 3:
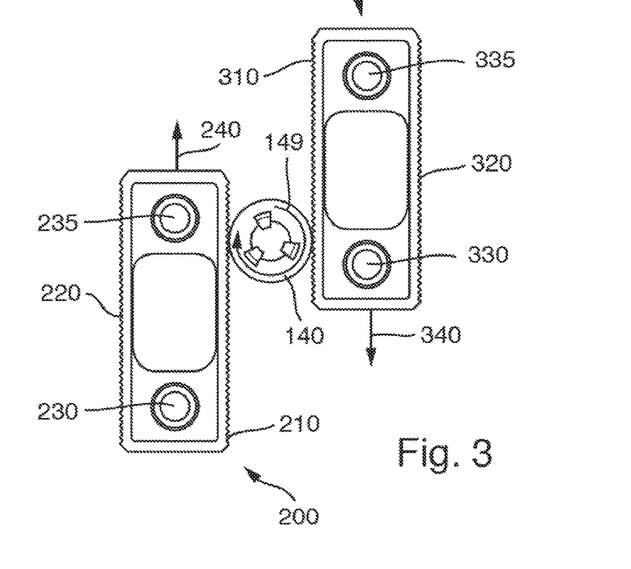
FIG. 3 illustrates the arrangement of FIG. 2 with the rotator elements abutting the sample container carrier according to an embodiment of the present disclosure.

In FIG. 3, the rotator elements 200, 300 have been moved such that the outer surface 142 of the sample container carrier 140 can abut the linear surfaces 210, 310, i.e. the first linear surfaces 210, 310 can respectively be in contact with the outer surface 142 of the sample container carrier 140.

In order to rotate the sample container carrier 140, the first rotator element 200 can be moved along a direction shown by an arrow 240 and the second rotator element 300 can be moved along a direction shown by an arrow 340. This can result in the exertion of respective rotating forces on the sample container carrier 140 leading to a rotation of the sample container carrier 140 as shown by an arrow 149. Thus, the sample container carrier 140 can be easily and reliably rotated by moving the rotator elements 200, 300 appropriately.

The fact that the first linear surfaces 210, 310 can be toothed can lead to increased friction between the rotator elements 200, 300 and the sample container carrier 140, which can simplify rotation.

The respective second linear surfaces 220, 320 may not be used in the shown embodiment. The rotator elements 200, 300 can also have been equipped with only one respective linear surface. However, it can be noted that the provision of two linear surfaces for each rotator element 200, 300 can increase flexibility of operation.

Figure 4:
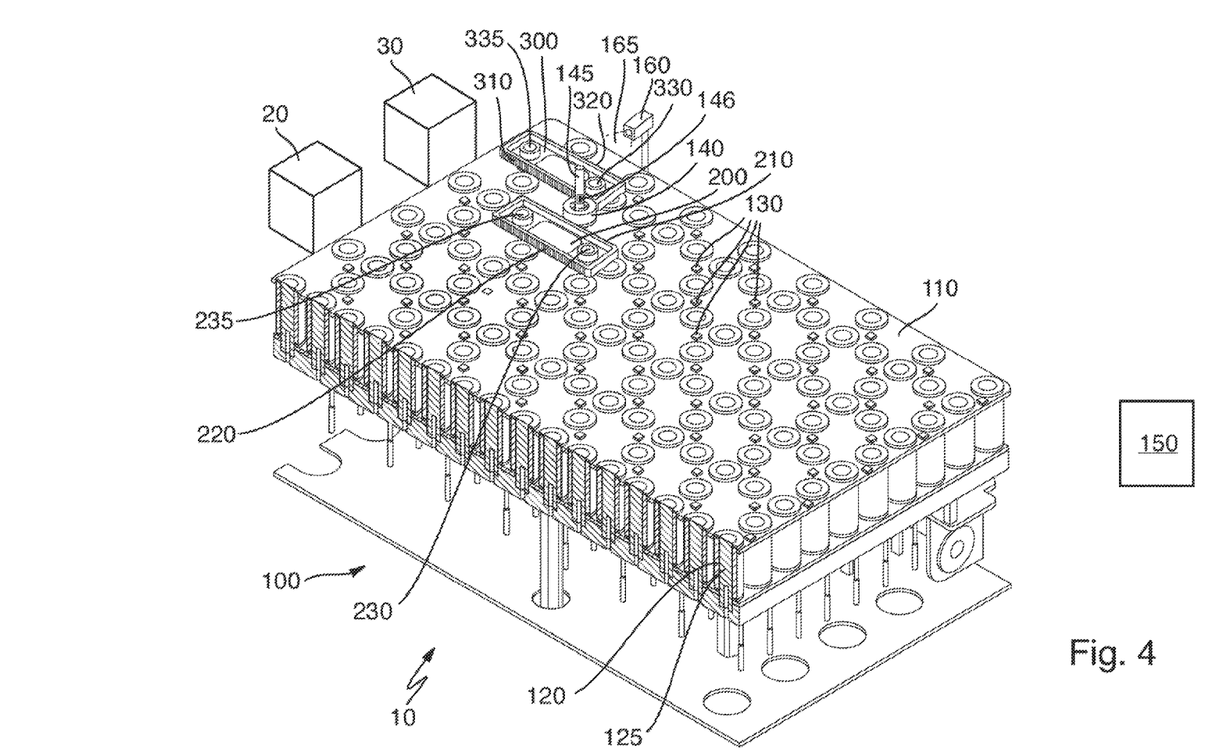
FIG. 4 illustrates a laboratory automation system according to an embodiment of the present disclosure.

FIG. 4 shows a laboratory automation system 10. The laboratory automation system 10 can comprise a first laboratory station 20, a second laboratory station 30 and a laboratory sample distribution system 100.

It can be noted that the laboratory stations 20, 30 are only shown exemplarily here, and that typical laboratory automation systems can comprise more than two laboratory stations.

The laboratory sample distribution system 100 can comprise a transport surface 110, on which elements such as a sample container carrier 140 or the rotator elements 200, 300 can be placed and can move.

Below the transport plane 110 a plurality of electro-magnetic actuators 120 can be arranged. Each electro-magnetic actuator 120 can comprise a ferromagnetic core 125. A number of position sensors 130, embodied as Hall sensors, are distributed over the transport plane 110.

The electro-magnetic actuators 120 and the position sensors 130 can all be electrically connected with a control device 150. The control device 150 can be configured to drive the electro-magnetic actuators 120 and to read out information from the position sensors 130.

The sample container carrier 140 can comprise a magnetically active device embodied as a permanent magnet. The permanent magnet is not visible in FIG. 4, because it can be located inside the sample container carrier 140.

The permanent magnet of the sample container carrier 140 can interact with magnetic fields generated by the electro-magnetic actuators 120. Thus, the control device 150 can move the sample container carrier 140 over the transport plane 110 in two dimensions using the electro-magnetic actuators 120.

The magnetic field generated by the permanent magnet of the sample container carrier 140 can also be detected by the position sensors 130. Thus, the control device 150 can monitor the position of the sample container carrier 140.

The sample container carrier 140 can carry a sample container 145. The sample container 145 can be embodied as a conventional laboratory sample tube being able to contain a sample, such as a blood sample.

It can be to be understood that the sample container carrier 140 is only shown exemplarily here, and that a typical laboratory sample distribution system 100 can comprise a plurality of such sample container carriers 140.

On the outer surface of the sample container 145 a barcode 146 can be located. The barcode 146 can give information about the sample contained in the sample container 145. For example, in the case of a medical sample data relating to a patient, a hospital or a suspected disease can be coded by the barcode 146.

In order to read out the barcode 146, the laboratory sample distribution system 100 can comprise a conventional barcode reading device 160 embodied as a camera. The barcode reading device 160 can be connected to the control device 150.

As depicted in FIG. 4, the barcode 146 may not be in a suitable orientation for being read by the barcode reading device 160. For that reason, the first rotator element 200 and the second rotator element 300 can be provided on the transport plane 110 to rotate the sample container carrier 140 until the barcode 146 can be read by the barcode reading device 160.

Due to the permanent magnets 230, 235, 330, 335, the control device 150 can move the rotator elements 200, 300 similarly to a sample container carrier 140. Thus, the control device 150 can move the rotator elements 200, 300 according to the concept shown and discussed with respect to FIG. 3 for rotating the sample container carrier 140. For that purpose, the control device 150 can be adapted to bring the rotator elements 200, 300 into contact with the sample container carrier 140 and to move them antiparallel to each other by driving the electro-magnetic actuators 120.

Thus, the sample container carrier 140 can be rotated using the rotator elements 200, 300 until the barcode 146 is visible by the barcode reading device 160. This can allow for easy and reliable readout of the barcode 146.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method of rotating a sample container carrier of a laboratory sample distribution system, wherein the laboratory sample distribution system comprises a number of sample container carriers, wherein the sample container carriers are adapted to carry one or more sample containers, wherein the sample containers comprise samples, at least one rotator element comprising a linear surface, a transport plane, wherein the transport plane is adapted to support the sample container carriers and the least one rotator element, a driver, wherein the driver is adapted to move the sample container carriers and the at least one rotator element on top of the transport plane, and a control device, wherein the control device is configured to control the driver such that the sample container carriers move over the transport plane along predetermined transport paths, the method comprising the steps:
   a) moving the sample container carrier and/or the at least one rotator element relative to each other on the transport plane such that the sample container carrier abuts the linear surface; and
   b) moving the sample container carrier and/or the rotator element relative to each other on the transport plane such that the linear surface exerts a rotating force on the sample container carrier.

2. The method according to claim 1, wherein the sample container carrier has a circular horizontal cross section.

3. The method according to claim 1, wherein in step b, the rotator element moves on the transport plane relative to the sample container carrier while the sample container carrier is held in a constant position on the transport plane.

4. The method according to claim 3, wherein in step a, a further rotator element comprising a further linear surface is moved on the transport plane such that the sample container carrier abuts the further linear surface and, in step b, the further rotator element is moved relative to the sample container carrier such that the further linear surface exerts a further rotating force on the sample container carrier, the further rotating force amplifying the rotating force.

5. The method according to claim 4, wherein the further rotator element is moved antiparallel to the rotator element.

6. The method according to claim 4, wherein the further rotator element is moved such that the further rotating force has the same magnitude as the rotating force.

7. The method according to claim 1, wherein in step b, the sample container carrier moves on the transport plane relative to the rotator element while the rotator element is held in a constant position on or besides the transport plane.

8. The method according to claim 1, wherein each linear surface is a knurled, toothed or rubber-coated surface.

9. The method according to claim 1, wherein the sample container carrier has a knurled, toothed or rubber-coated outer surface abutting the linear surface.

10. The method according to claim 1, wherein in step b, the sample container carrier is rotated in a field of view of a barcode reading device until a barcode being located on the sample container or on the sample container carrier is facing towards the barcode reading device.

\* \* \* \* \*